(12) United States Patent  
Bruschweiler et al.

(10) Patent No.: US 7,835,872 B2  
(45) Date of Patent: Nov. 16, 2010

(54) ROBUST DECONVOLUTION OF COMPLEX MIXTURES BY COVARIANCE SPECTROSCOPY

(75) Inventors: Rafael Bruschweiler, Tallahassee, FL (US); Fengli Zhang, Tallahassee, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 260 days.

(21) Appl. No.: 12/032,903

(22) Filed: Feb. 18, 2008

(65) Prior Publication Data

US 2008/0201087 A1 Aug. 21, 2008

Related U.S. Application Data

(60) Provisional application No. 60/890,449, filed on Feb. 16, 2007.

(51) Int. Cl.  
*G01N 31/00* (2006.01)  
*G06F 17/18* (2006.01)

(52) U.S. Cl. .......... 702/22; 702/179; 702/180; 702/181

(58) Field of Classification Search .......... 702/22, 702/179–194  
See application file for complete search history.

(56) References Cited

U.S. PATENT DOCUMENTS

2004/0214348 A1 * 10/2004 Nicholson et al. .......... 436/518

* cited by examiner

*Primary Examiner*—Mohamed Charioui  
*Assistant Examiner*—Phuong Huynh  
(74) *Attorney, Agent, or Firm*—Sutherland Asbill & Brennan LLP

(57) ABSTRACT

Methods and systems are provided for the deconvolution of the NMR spectrum of a mixture into individual components and spin systems by combining covariance total correlation spectroscopy (TOCSY) spectra with covariance NMR. The method may include obtaining a 2D TOCSY spectra of a chemical mixture and then performing a series of analytical steps to identify the individual components of the mixture.

20 Claims, 8 Drawing Sheets

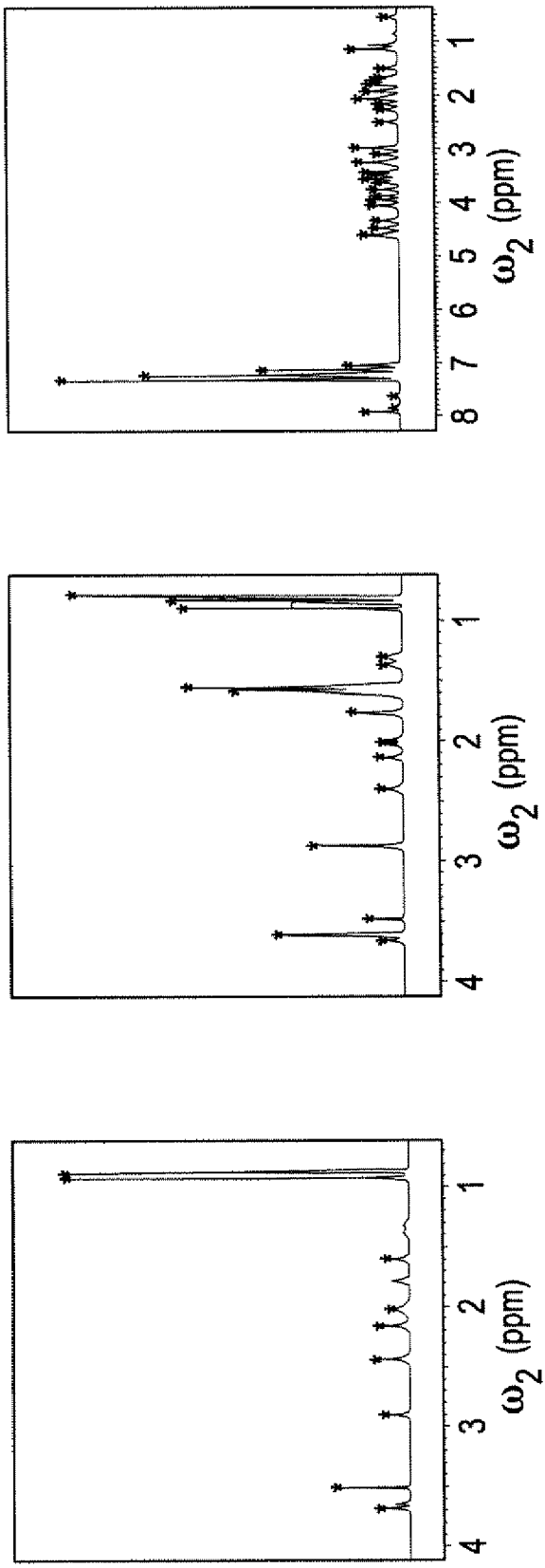

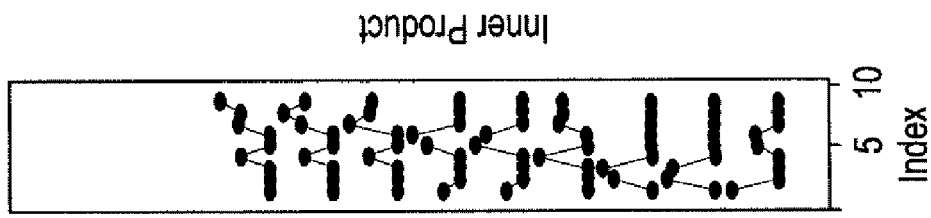
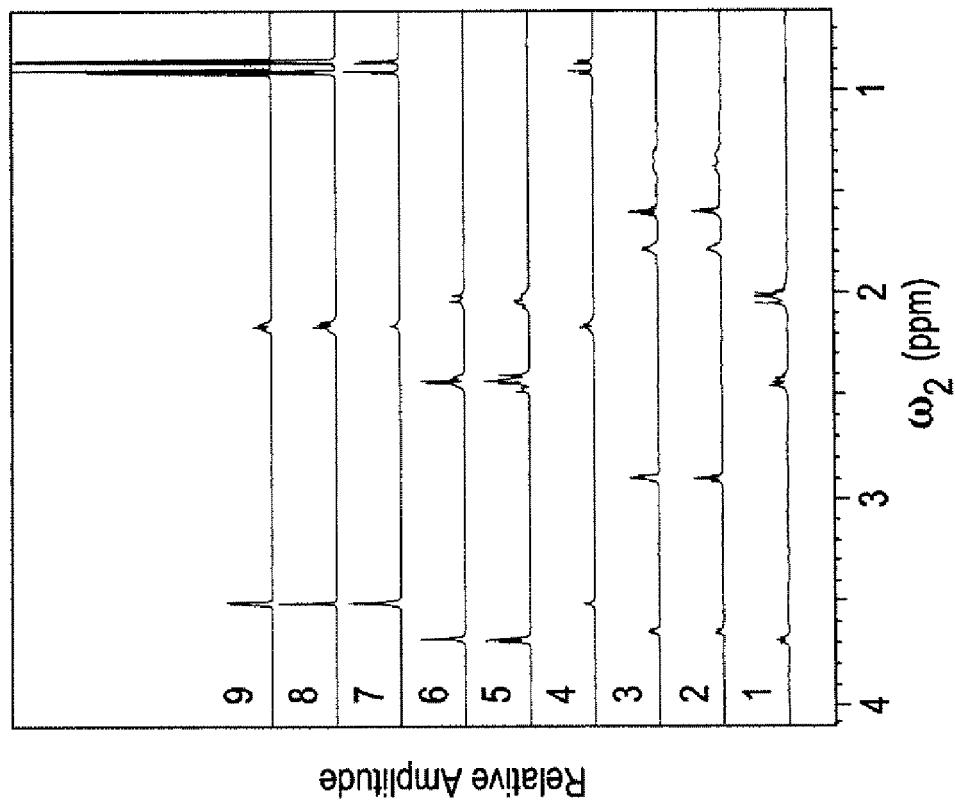
FIG. 2A
FIG. 2B

ROBUST DECONVOLUTION OF COMPLEX MIXTURES BY COVARIANCE SPECTROSCOPY

CROSS-REFERENCE TO RELATED APPLICATIONS

This application claims the benefit of U.S. Provisional Application No. 60/890,449, filed Feb. 16, 2007. The application is incorporated herein by reference in its entirety.

STATEMENT REGARDING FEDERALLY SPONSORED RESEARCH OR DEVELOPMENT

This invention was made with government support under National Institutes of Health Grant No. R01 GM 066041. The government has certain rights in the invention.

BACKGROUND OF THE INVENTION

This disclosure relates generally to chemical analysis methods, and more particularly to the identification of chemical components in a mixture using nuclear magnetic resonance spectra.

Reliable analysis of complex mixtures plays a critical role in many areas of chemistry and the life sciences; however, the identification of components in chemical mixtures, such as different solutes in a solution, remains a fundamental problem in many areas of chemistry. The recent advent of metabolomics has generated a critical demand for powerful analysis methods of fluid mixtures for the food and life sciences. While important progress is being made in potentially laborious and costly hyphenation methods, spectroscopic methods have the power to circumvent or reduce the need for hyphenation prior to analysis. See Christophoridou, et al., *J. Agric. Food Chem.* 53, 4667-4679 (2005).

Most compounds contain multiple NMR active spins that are J-coupled, thereby allowing the identification of spin-spin coupling networks for the discrimination between components as well as their subsequent identification by screening against a database. Particularly useful in this regard is the 2D NMR $^1$H-$^1$H TOCSY experiment, which monitors multiple relay transfers of spin magnetization within a spin system to provide a wealth of scalar spin-spin coupling connectivity information at a high sensitivity. Braunschweiler & Ernst, *J. Magnetic Resonance* 53, 521 (1983).

An unsupervised deconvolution method recently was proposed using principal component analysis (PCA) of the covariance TOCSY spectrum of a mixture. Zhang & Brüschweiler, *Chemphyschem.* 5, 794-796 (2004). In the absence of significant spectral overlap, the dominant PCA eigenmodes well approximate the 1D spectra of the individual components. However, increasing amounts of spectral overlaps between components results in "mixed modes" whose assignment to known compounds can pose a significant challenge. It would be desirable to provide a method to overcome these and other limitations.

SUMMARY OF THE INVENTION

Embodiments provided herein include a method for the deconvolution of an NMR spectrum of a chemical mixture. In one embodiment, the method comprises the steps of:
obtaining a 2D TOCSY spectra of a chemical mixture;
performing covariance processing on the 2D TOCSY spectra to determine a matrix square root of the covariance spectrum (C);
evaluating similarity or overlap of each row vector ($c_i$) and column vector ($c_j$) of the covariance spectrum (C) to form an overlap matrix (O) with elements ($O_{ij}$);
calculating an importance index (vector P with elements $P_j$) from the overlap matrix (O) by co-adding the elements ($O_{ij}$) of the overlap matrix (O);
identifying a subset of rows of interest by applying standard peak picking to the importance index (P);
clustering the subset of rows of interest to identify a unique set of spin systems and compounds;
displaying the unique set of spin systems and compounds as corresponding traces of the covariance matrix to create a final set of magnitude traces; and
identifying and assigning each individual component of the chemical mixture from the final set of magnitude traces.

Also provided in embodiments herein are systems and apparatus for the deconvolution of complex mixtures by covariance spectroscopy. In one embodiment, the system comprises a Nuclear Magnetic Resonance (NMR) System for producing a 2D TOCSY spectrum and a means for deconvolution of the 2D TOCSY spectrum.

BRIEF DESCRIPTION OF THE FIGURES

FIGS. 1D-F are illustrations of the importance index vector (P) for Samples I, II, and III, respectively.

FIG. 2A represents the nine traces of covariance TOCSY spectrum of Sample I picked according to importance index of FIG. 1D and sorted according to the intensities in FIG. 1D.

FIG. 2B represents the normalized inner products among the 9 traces of covariance TOCSY spectrum of Sample I.

DETAILED DESCRIPTION OF THE PREFERRED EMBODIMENTS

Figure 1A:
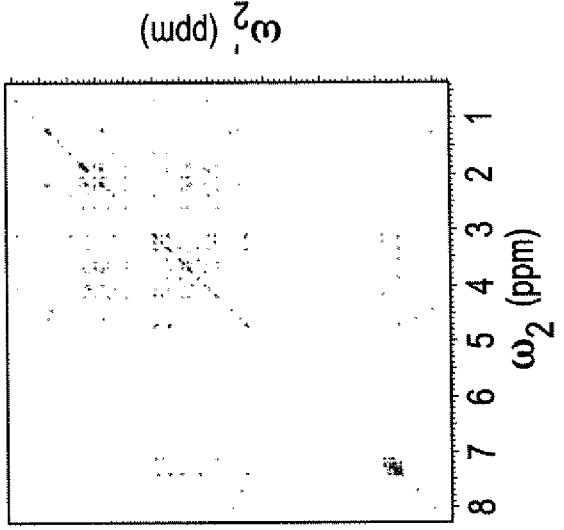
FIGS. 1A-C are the covariance NMR TOCSY spectra of (1A) a three amino acid mixture containing the amino acids Glu, Lys, Val (Sample I), (1B) a four amino acid mixture containing the amino acids Glu, Leu, Lys, Val (Sample II), and (1C) the cyclic decapeptide antamanide (Sample III).

Methods have been developed, termed DemixC (C stands for clustering), to overcome the above-identified limitations by identifying for each component characteristic traces that are essentially free of overlaps, therefore allowing identification and assignment with high confidence. These methods provide a new analytical tool for the deconvolution of the NMR spectrum of a mixture into individual components and spin systems. These methods do not require hyphenation and are based on covariance total correlation spectroscopy (TOCSY) spectra. Because experimental efficiency is desirable for high-throughput applications, TOCSY may be combined with covariance NMR, which produces high-resolution spectra Largely independent of the number of increments along the indirect time domain $t_1$.

In one embodiment, a method is provided for the deconvolution of the NMR spectrum of a mixture. The method generally comprises obtaining a 2D TOCSY spectra of a chemical mixture followed by a series of analytical steps to identify the individual components of the mixture. For example, such analysis may be conducted by performing covariance processing on the 2D TOCSY spectra to determine the matrix square root of the covariance spectrum (C); evaluating the similarity or overlap of each row vector ($c_i$) and column vector ($c_j$) of the covariance spectrum (C) to form an overlap matrix (O) with elements ($O_{ij}$); calculating the importance index (vector P with elements $P_j$) from the overlap matrix (O) by co-adding the elements ($O_{ij}$) of the overlap matrix (O); identifying a subset of rows of interest by applying standard peak picking to the importance index (P); clustering the subset of rows of interest to identify a unique set of spin systems and compounds; creating a final set of magnitude traces from the unique set of spin systems; and identifying and assigning the individual components of the mixture from the final set of magnitude traces. Exemplary embodiments of the method for the deconvolution of the NMR spectrum of a mixture are described in more detail hereinbelow.

Methods for obtaining 2D TOCSY data sets and for covariance processing of such data sets are known in the art. Generally, the step of covariance processing is performed in the mixed-time frequency domain as described in N. Trbovic, et al., *J. Magnetic Resonance* 171, 277-283 (2004).

In one embodiment of the step of covariance processing on 2D TPPI TOCSY datasets, the time-domain data is (1) Fourier transformed along the direct dimension $t_2$, (2) phase- and baseline corrected, (3) followed by elimination of the dispersive part, and (4) subjected to singular value decomposition (SVD) to determine the matrix square-root of the covariance spectrum (C).

In another embodiment of the step of covariance processing on 2D TPPI-States TOCSY datasets, the cosine and sine $t_1$ modulated parts of the time-domain data are (1) Fourier transformed along the direct dimension $t_2$, (2) phase corrected, (3) followed by elimination of the dispersive parts, and (4) subjecting the cosine and the sine modulated parts to SVD individually before they are co-added to determine the square-root of the covariance spectrum (C). As is characteristic for covariance NMR, the resulting spectra for both of the covariance processing steps described above are fully symmetric, displaying the same high spectral resolution along both dimensions.

Following the covariance processing of the 2D TOCSY datasets, the similarity or overlap ($O_{ij}$) between each row vector ($c_i^T$) and column vector ($c_j$) of the square root of the covariance spectrum (C) may be determined. The inner product between these vectors (traces) represents a suitable metric of similarity (Formula 1):

$$O_{ij} = c_i^T \cdot c_j \qquad (1)$$

or, in matrix notation (Formula 2), $$O = C^T \cdot C \qquad (2)$$

wherein O is the defined as the 'overlap matrix' comprising elements $O_{ij}$. Larger elements ($O_{ij}$) indicate higher degrees of overlap, and therefore also greater similarity of the covariance TOCSY traces represented by the row and column vectors ($c_i$ and $c_j$, respectively). Prior to the overlap calculation, the diagonal peaks may be replaced by a Gaussian peak with the amplitude of the largest non-diagonal peak in the same column or row as the diagonal peaks. This replacement generally may be desirable due to the diagonal peaks tendency to have a disproportionately large amplitude that dominate the inner products, which results in a modified overlap matrix (O') for which the influence of the diagonal of the covariance spectrum is diminished.

Following creation of the modified overlap matrix (O'), the elements of each column of the modified overlap matrix may be co-added to determine the importance index, represented by a vector (P) comprising elements ($P_j$) (Formula 3):

$$P_j = \Sigma O'_{ij} \qquad (3)$$

$P_j$ is a quantitative measure for the cumulative overlap between the TOCSY trace (column or row) at frequency $\omega_j$ with all other traces (columns or rows). A large component $P_j$ indicates that the covariance TOCSY column j has strong overlaps with other rows, whereas a low $P_j$ value reflects little overlap. Overlaps stem from rows belonging to other spins of the same spin system as well as rows of other spin systems whose resonances overlap with the resonances of row j. Vectors that belong to the same spin system have resonances at the same positions, provided that the distribution of magnetization via isotropic mixing during the TOCSY experiment is sufficiently uniform among the spins.

Standard peak picking then may be applied to P in order to identify a subset of rows of interest based on their importance. This involves the determination of local maxima above a given threshold. In one embodiment, this threshold should be larger than the noise floor and can be adjusted to exclude weak traces that are not of interest. This yields a list of rows of the covariance TOCSY spectrum representing a small subset of all traces.

The subset of rows identified by standard peak picking then may be clustered, based on the mutual overlaps of the normalized rows of C ($O'_{N,ij}$) to identify a unique set of spin systems and compounds.

The resulting clustered subset of rows of interest then may be displayed as the corresponding traces of the covariance matrix with the original diagonal peak scaled such that it is identical to the maximal off-diagonal peak in the same trace. This final set of magnitude traces represents the individual components of the mixture that may be identified and assigned, for example, by screening against a spectral database.

The analysis of mixtures by the DemixC method described herein is based on the abundant spin connectivities in total correlation spectroscopy, providing an efficient means for the spectral identification of spin systems and their compounds. The covariance nature of the spectrum ensures high resolution along both frequency dimensions.

Covariance TOCSY fundamentally differs from STOCSY in that it uses covariances over 1D spectra with different $t_1$ evolution times of the same sample, whereas in STOCSY covariances are computed over 1D spectra of different samples. See e.g., Holmes, et al. *J. Proteome Res.* 5, 1313 (2006) and Cloarec, et al. *Anal. Chem.* 77, 1282 (2005).

A previous method based on principal component analysis (PCA) required a series of TOCSY spectra recorded with different mixing times. See Zhang & Brüschweiler, *Chemphyschem* 5, 794-796 (2004). The present methods, however, do not require use of different mixing times provided that the chosen mixing time is long enough to allow sufficient magnetization transfer throughout the whole spin system. In one embodiments of the present methods, the mixing times may be in the range of about 60 ms and about 100 ms. Longer mixing times are feasible; however, relaxation effects may cause a reduction in the signal-to-noise.

Other considerations also may be made for compounds that contain multiple spin systems (i.e., spin systems that are disconnected from each other), such as the individual amino acids of antamanide. In multiple spin systems, each spin system yields an independent trace as if it belonged to an individual molecule. Accordingly, this property of the TOCSY experiment needs to be taken into account. The DemixC method may identify the best candidates for individual spin system traces based on their importance index as determined by the sum of the overlaps with all other candidate traces. Traces with a low to medium importance index are more likely to represent individual spin systems, whereas traces with a large importance index are more likely to be prone to overlap. The previously disclosed PCA method, conversely, tends to represent overlapping spin systems by some of the largest modes which results in "mixed modes" (i.e., modes that represent a superposition of spectra of multiple spin systems) and "compensatory modes" (modes that correct for non-uniform spin excitation effects). These modes can be difficult to interpret as they do not correspond to individual 1D spectra and impede the analysis of more complex mixtures.

Extreme resonance overlap may impose natural restrictions. For example, if all resonances of a certain compound overlap with resonances of other systems, then the deconvolution method may not result in definitively identifying the compound. See for example, Sample III in the Examples, where Phe 9 of antamanide represents such a case. Although the deconvolution procedure may produce the correct result, the trace selection may become ambiguous when the number of overlaps of a component is very large.

The present DemixC deconvolution methods take full advantage of the high spectral resolution and redundant connectivity information of covariance TOCSY spectra. Trace analysis based on the importance index and subsequent clustering is highly efficient and remarkably robust at providing individual 1D spectral information of the underlying spin systems.

In another aspect, apparatus and systems are provided for the deconvolution of complex mixtures by covariance spectroscopy. The apparatus generally may include a spectrum producing apparatus known in the art, such as a Nuclear Magnetic Resonance (NMR) System, operatively coupled with a means for deconvolution of the spectrum. Suitable means for deconvolution of the spectrum may include computational systems composed of appropriate hardware and software capable of processing the spectra as described herein and carrying out the present DemixC deconvolution methods described herein. For instance, the means for deconvolution may include the MATLAB programming environment (Mathworks, Natick, Mass.).

The present DemixC deconvolution methods provide an efficient and reliable means for identifying the individual components of complex mixtures without requiring the physical separating of the complex mixtures. Accordingly, these methods may be applied in any situation which requires characterization of complex chemical and/or biological mixtures. In one aspect, the present DemixC deconvolution methods may be applied to the analysis of biofluids and tissue extracts for the identification and quantification of biologically active molecules or in metabolomics, biomarker identification, and diagnosis and therapy of diseases.

The devices, systems, and methods described above will be further understood with reference to the following non-limiting examples.

EXAMPLES

The DemixC method was demonstrated using three samples of variable complexity. Sample I consisted of the 3 amino acids Glu, Lys, and Val dissolved in $D_2O$. Sample II consisted of the 4 amino acids Glu, Leu, Lys, and Val in $D_2O$. The amino acid concentrations of both Samples I and II was 7 mM. Sample III contained the cyclic decapeptide antamanide [-Val-Pro-Pro-Ala-Phe-Phe-Pro-Pro-Phe-Phe-] dissolved in deuterated chloroform at a concentration of 1 mM. Wieland & Faulstich, *Crit. Rev. Biochem.* 5, 185 (1978). While the dissolved peptide of Sample III was not an actual mixture, in terms of its proton NMR properties it behaved like a mixture of 10 amino acids at 1 mM concentration each. The low variability of the amino acid composition (4 phenylalanines and 4 prolines) leads to significant resonance overlap, providing a rigorous test case for the performance of the method.

Two-dimensional TOCSY experiments for Samples I and II were recorded at 600 MHz with mixing times ($\tau_m$) of 97 ms and 62 ms, respectively, with 2048 complex points in $t_2$ and 1024 points in $t_1$ in TPPI mode. TOCSY spectra of Sample III were recorded at 800 MHz with mixing times ($\tau_m$) of 97 ms or 76 ms with 2048 complex points in $t_2$ and 512 complex points in $t_1$ in TPPI-States mode. The TOCSY mixing sequence was MLEV-17 for all three mixtures. Bax & Davis, *J. Magn. Reson.*, 65, 335 (1985). All NMR experiments were carried out at 298 K.

The compounds underlying the selected cross sections were identified by comparison with 1D spectra contained in a NMR databank. For Samples I-III, the metabolomics/metabonomics part of the Biological Magnetic Resonance Data Bank (BMRB) (http://www.bmrb.wisc.edu/metabolomics/) was used.

Sample I

The DemixC method first was demonstrated for Sample I, which contained amino acids E, K, and V. Zhang & Brüschweiler, *Angewandte Chemie* (2007). The covariance NMR TOCSY spectrum is shown in FIG. 1A. The importance index vector P then was constructed from O' (FIG. 1D). The 9 cross sections (rows) in the covariance spectrum C were identified (peak positions marked by filled circles in FIG. 1D) and plotted in FIG. 2A. The mutual overlaps $O'_{N,ij}$ between the 9 rows are shown in FIG. 2B. The higher a $O'_{N,ij}$ value, the more similar were the corresponding rows i and j. Those of ordinary skill in the art should appreciate that due to redundant connectivity information available in TOCSY spectra, selection of peak positions does not require that all traces belonging to a certain spin system be picked in the importance index profile without having an adverse effect on the deconvolution result. For example, the threshold of the covariance spectrum in FIG. 1D was set such that traces around 1.35, 1.80 and 3.65 ppm were not selected.

Figure 3B:
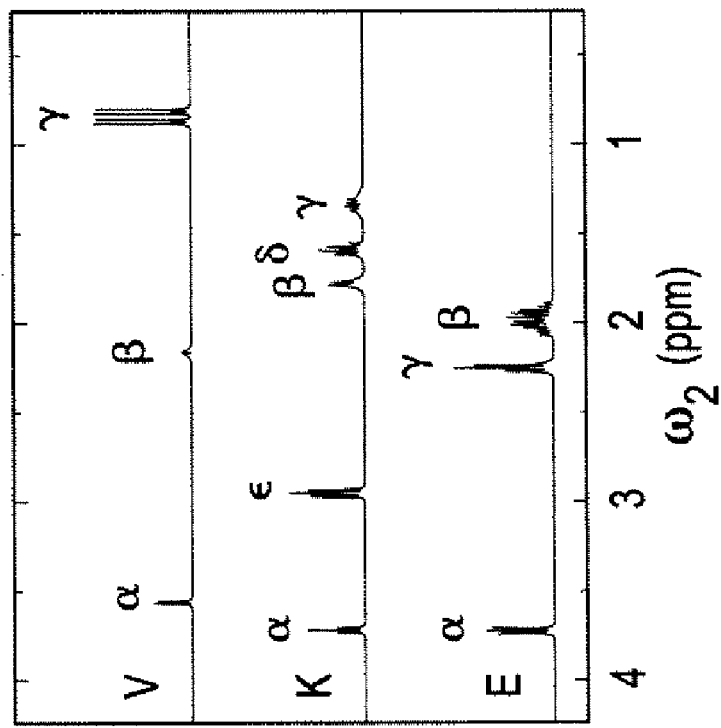
FIGS. 3A-D illustrate the results of the DemixC deconvolution method for Sample I (3A) and Sample II (3C) as compared to the 1D NMR spectra of the individual amino acids taken from the BMRB data bank for Sample I (3B) and Sample II (3D).
Figure 3A:
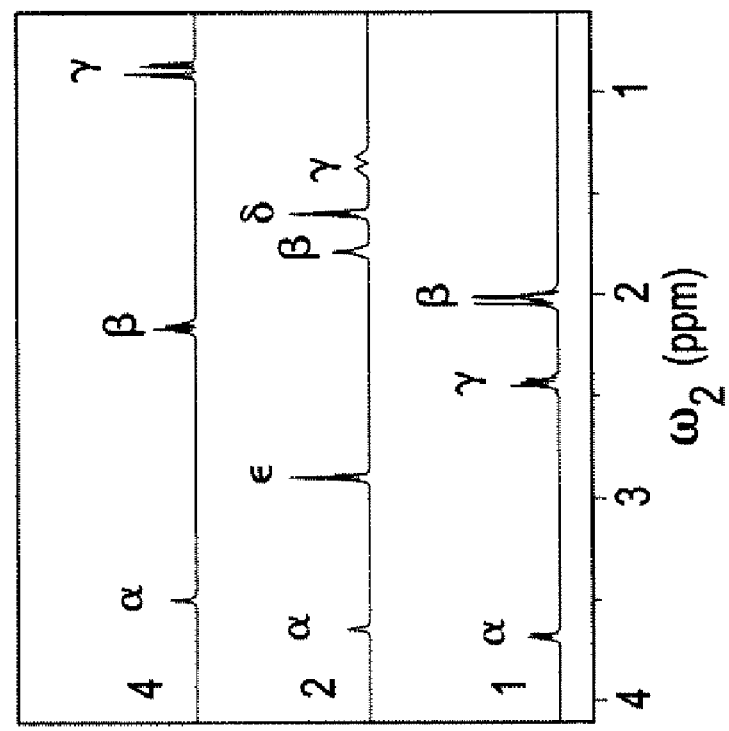

Basic clustering of the overlaps immediately revealed that rows 1, 5, and 6 represent the same compound (or spin system), rows 2 and 3 represent a 2nd compound, and rows 4, 7, 8, and 9 represent a 3rd compound. Because all 9 rows can be assigned to one of the three clusters, it follows that the TOCSY spectrum of Sample I contained no other detectable compound. The three clusters are represented by the trace spectra 1, 2, 4 (FIG. 3A). The proton 1D spectra contained in the BMRB for the 3 amino acids E, K, and V (FIG. 3B) were compared with the cluster representatives (FIG. 3A). The correspondence between the covariance traces and the BMRB spectra was good. Even the peak multiplets showed good agreement. Not wishing to be bound by any theory, the relative peak intensity differences may stem from non-uniform TOCSY transfer, differential relaxation effects, and from the scaling of the diagonal part of the covariance TOCSY traces. In addition, and again not wishing to be bound by any theory, the differences in resolution and multiplet patterns for the $H_\gamma$ protons of Lysine (FIGS. 3A and 3B) are believed to be due to the differences in magnetic field strengths used for the reference spectra (400 MHz) and the Sample II spectra (600 MHz).

In the absence of overlaps between resonances belonging to different spin systems, as was the case for Sample I, TOCSY traces for spins of the same spin-system reflected the 1D spectrum of the spin system and therefore contained equivalent information.

Sample II

Figure 1B:
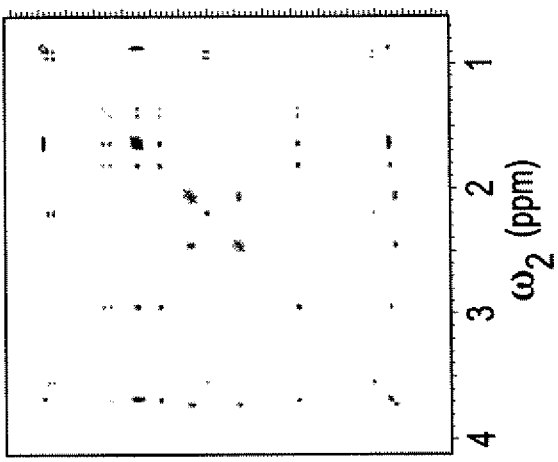
Figure 3D:
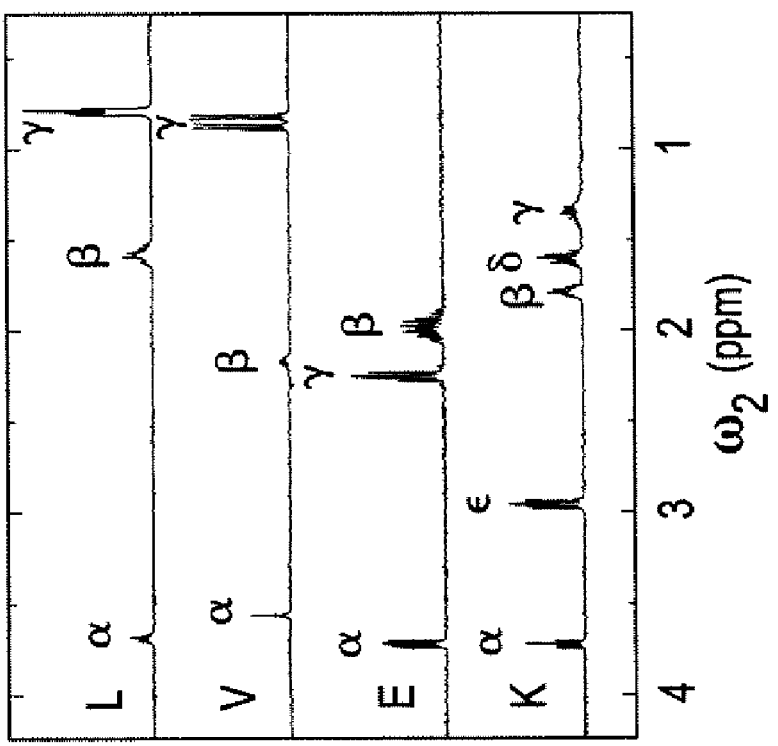
Figure 3C:
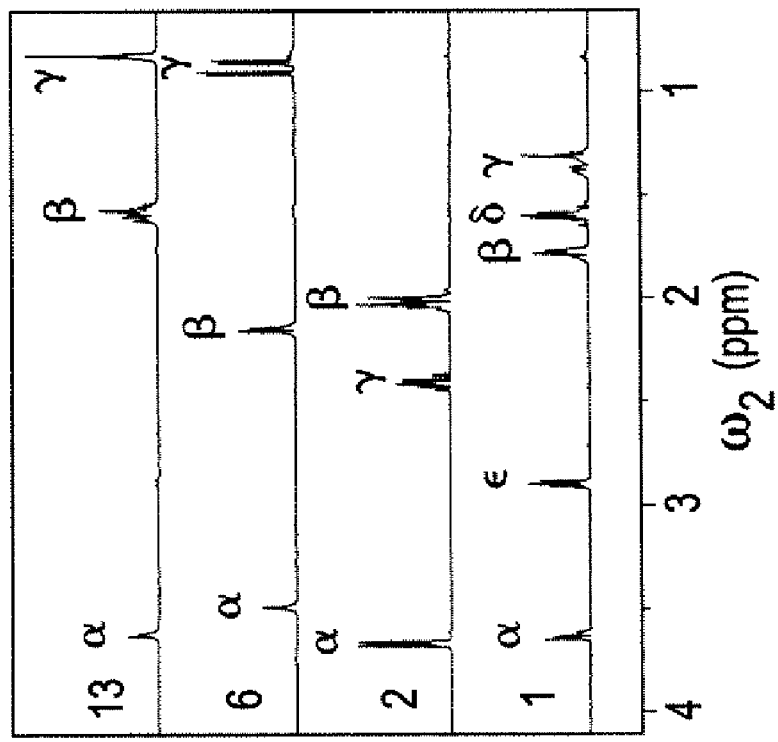

Sample II contained Leu as a fourth amino acid in addition to the three amino acids included in Sample I (Glu, Lys, and Val). This mixture showed significant peak overlap, particularly between the Leu and Lys spin systems (FIG. 1B). The importance index vector was constructed and peak positions identified (FIG. 1E) before identification of four clusters of traces (not shown). The representative trace for each cluster (FIG. 3C) was chosen to have a minimal importance index (FIG. 1E), ensuring selection of those traces that had low overlap with other spin systems. As shown in FIGS. 3B and 3C, the selected traces (FIG. 3C) agreed well with the BMRB spectra of these components (FIG. 3D).

Sample III

Figure 1C:
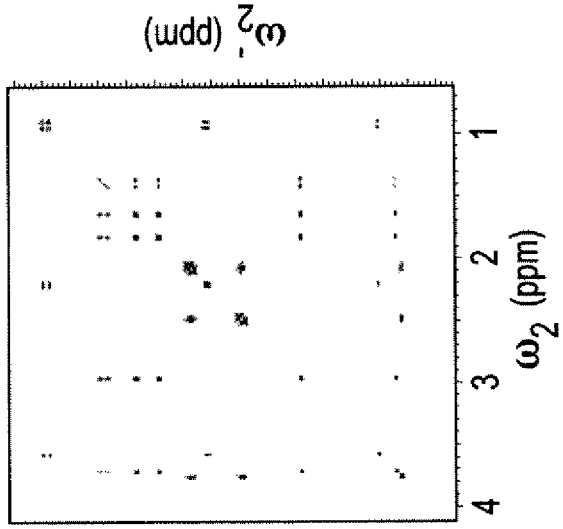
Figure 5A:
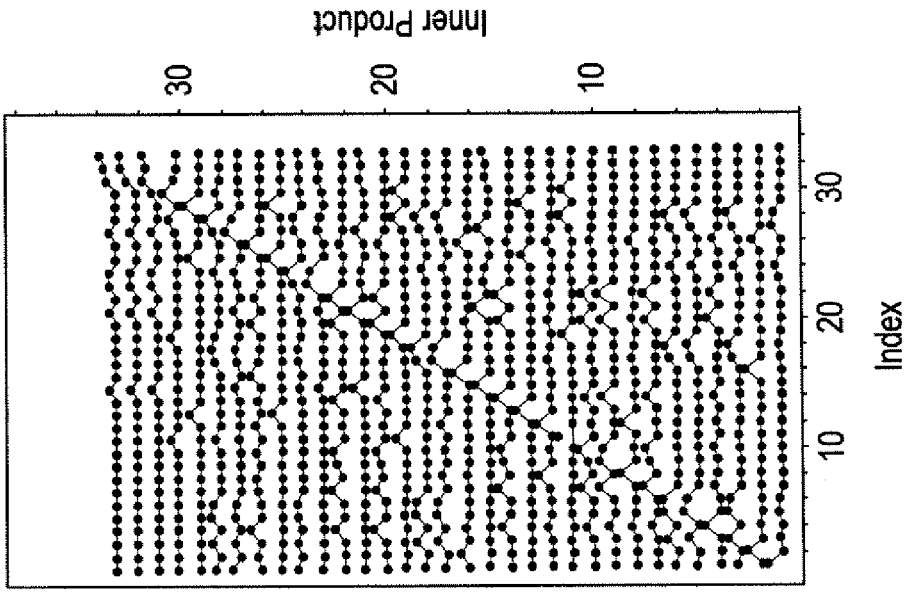
FIG. 5A represents the traces of covariance TOCSY spectrum of Sample III picked according to importance index of FIG. 1F and sorted according to the intensities in vector P.
Figure 5B:
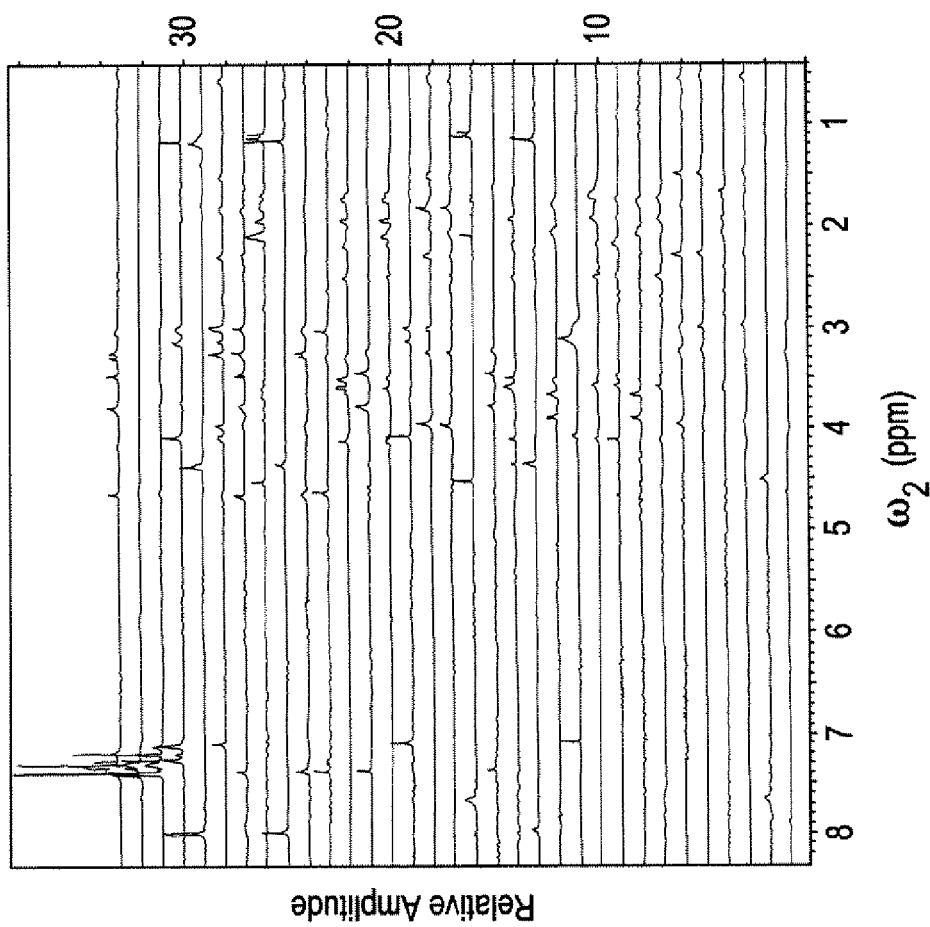
FIG. 5B represents the normalized inner products among the traces of covariance TOCSY spectrum of Sample III.

Application of the algorithm to the cyclic decapeptide antamanide provided a stringent test of the deconvolution method. The ten amino acids led to the rich covariance spectrum shown in FIG. 1C that exhibited substantial peak overlaps. Peak picking of the importance vector (FIG. 1F) yielded the 33 trace vectors shown in FIGS. 5A and 5B (sorted according to the intensities of the importance index vector P) together with their mutual overlap matrix. Inspection of the traces revealed numerous regions with strong overlap.

Figure 4:
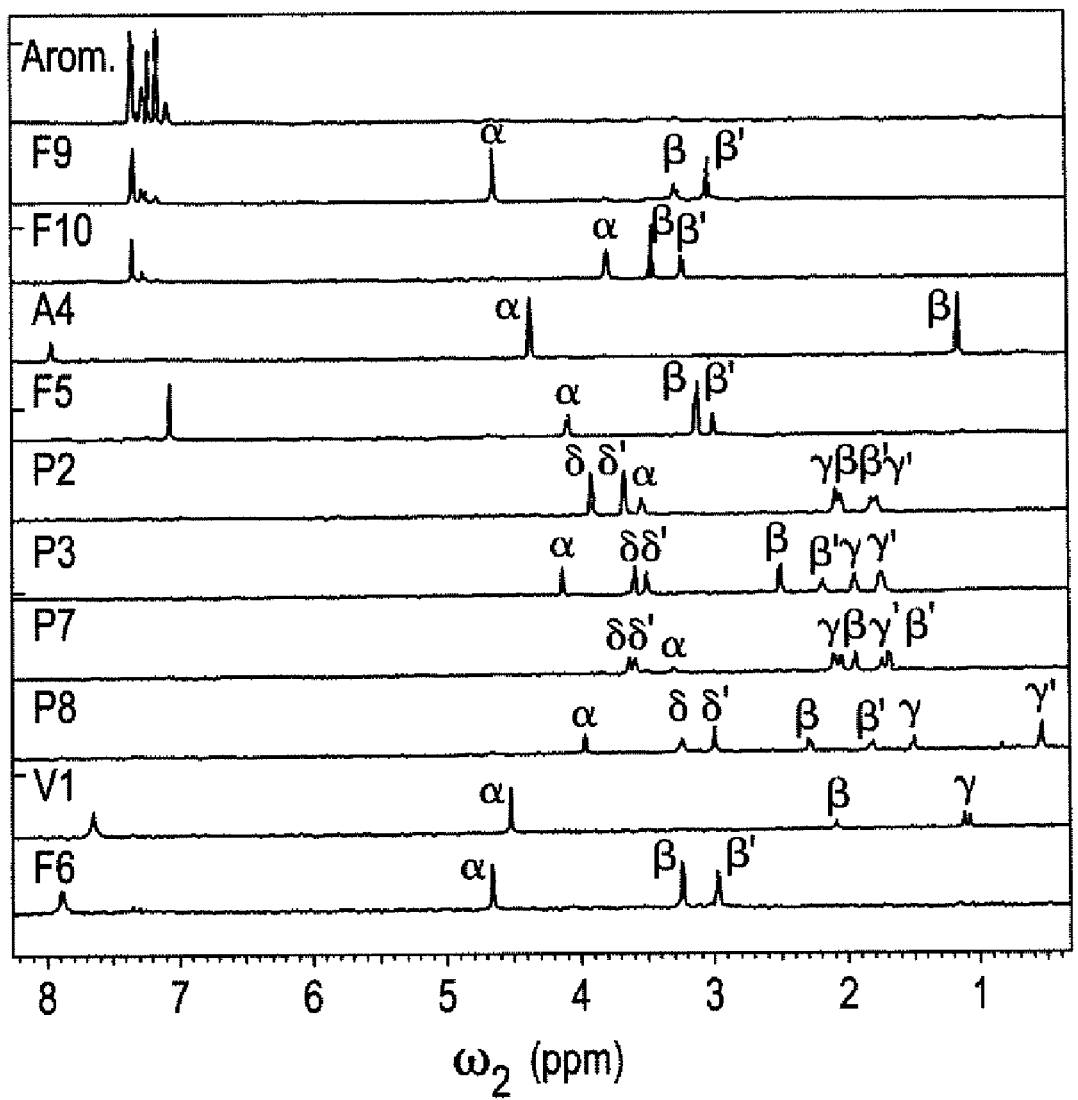
FIG. 4 illustrates the results of the DemixC method for Sample III.

Cluster analysis yielded the 11 representative traces depicted in FIG. 4. The 10 bottom traces corresponded to the amide and aliphatic proton resonances of the 10 amino acids while top trace (FIG. 4) represented the strongly overlapping aromatic resonances of the phenylalanine rings. The amino acid traces of FIG. 4 were fully consistent with the assignments of antamanide. See Wieland & Faulstich, *Crit. Rev. Biochem.* 5, 185 (1978).

The traces of Ala (A4) and Val (V1) were identified easily as set forth in Samples I and II. The four Phe (F5, F6, F9, and F10) and four Pro (P2, P3, P7, and P8) residues showed significant variability in their chemical shifts, likely due to structural and dynamic differences. See Bremi, et al., *J. Am. Chem. Soc.* 119, 4272 (1997); Kessler, et al., *J. Am. Chem. Soc.* 110, 3393 (1988); Madi, et al., *J. Am. Chem. Soc.* 112, 2908 (1990); Blackledge, et al., *Biochemistry* 32, 10960 (1993); Schmidt, et al., *J. Am. Chem. Soc* 115, 8747 (1993). The residue that overlapped most severely was F9: its α, β, β' protons fully or partially overlapped with the ones of F6 and its $H^N$ proton overlapped with the one of F10. Nonetheless, the DemixC protocol succeeded in finding a representative trace of this residue.

Figure 6:
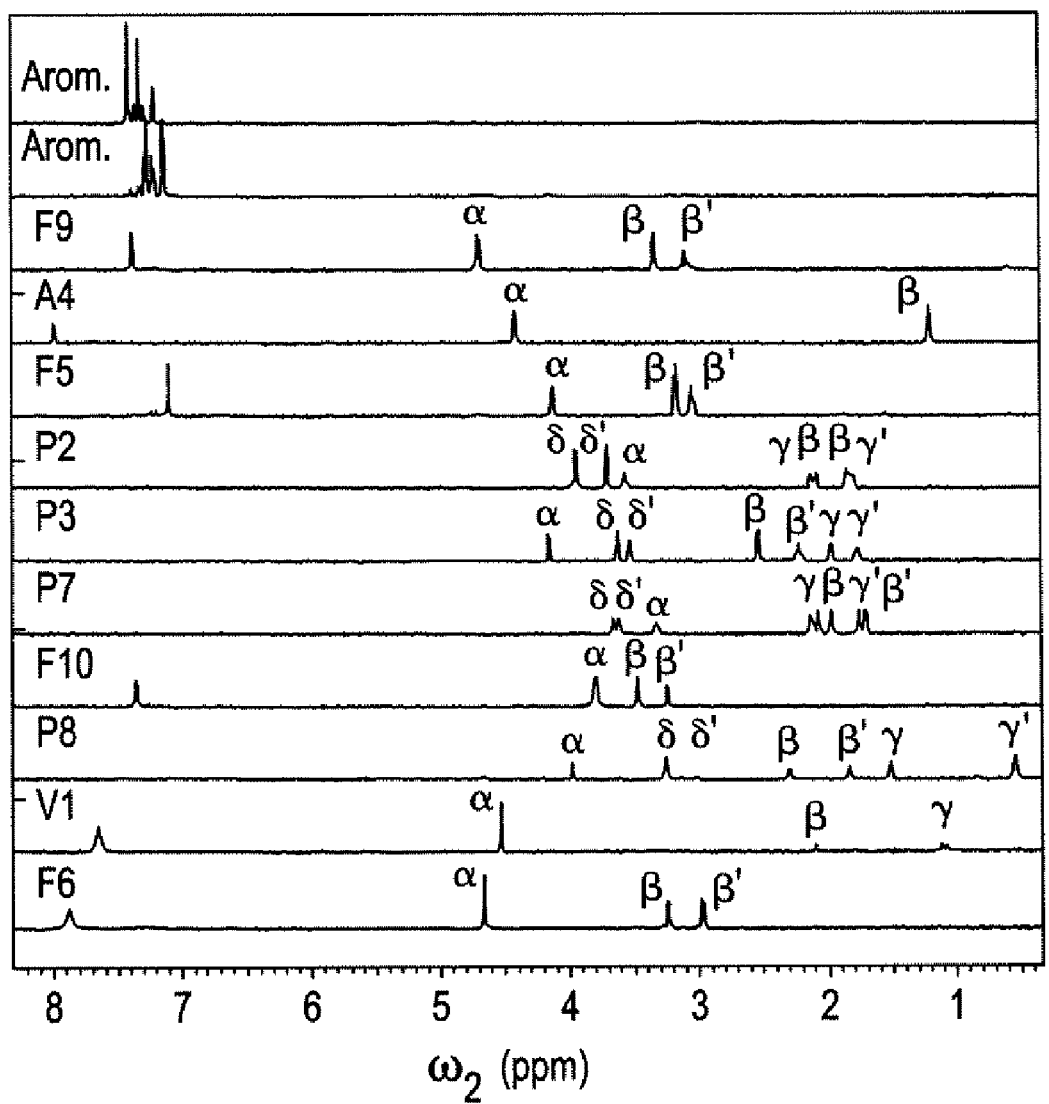
FIG. 6 represents the traces of covariance TOCSY spectrum of Sample III picked according to importance index and sorted according to the intensities in vector P for a reduced mixing time.

The spins systems of the aliphatic protons of all 10 amino acids also were correctly identified when the mixing time was reduced from 97 ms to 76 ms (FIG. 6), indicating that the exact mixing time is not critical provided that the mixing is sufficient to allow magnetization transfer throughout the whole spin system.

These examples illustrate that the DemixC method's effectiveness at the semi-automated side-chain assignment of peptides and small proteins. As small molecule NMR databases are rapidly growing, traces identified in covariance TOCSY spectra can be automatically screened against these databases to identify and quantify the TOCSY traces offering a path for the deconvolution of complex biological mixtures that is both efficient and reliable.

Publications cited herein and the materials for which they are cited are specifically incorporated herein by reference. Modifications and variations of the methods and devices described herein will be obvious to those skilled in the art from the foregoing detailed description. Such modifications and variations are intended to come within the scope of the appended claims.

We claim:

1. A method for the deconvolution of an Nuclear Magnetic Resonance Spectroscopy spectrum of a chemical mixture comprising the steps of:
    obtaining a two-dimensional total correlation spectroscopy spectrum of a chemical mixture;
    performing covariance processing on the two-dimensional total correlation spectroscopy spectrum to determine a matrix square root of the covariance spectrum (C);
    evaluating similarity or overlap of each row vector ($c_i$) and column vector ($c_j$) of the covariance spectrum (C) to form an overlap matrix (O) with elements ($O_{ij}$);
    calculating an importance index (vector P with elements $P_j$) from the overlap matrix (O) by co-adding the elements ($O_{ij}$) of the overlap matrix (O);
    identifying a subset of rows of interest by applying standard peak picking to the importance index (P);
    clustering the subset of rows of interest to identify a unique set of spin systems and compounds;
    displaying the unique set of spin systems and compounds as corresponding traces of the covariance matrix to create a final set of magnitude traces; and
    identifying and assigning each individual component of the chemical mixture from the final set of magnitude traces,
    wherein the steps are performed by a Nuclear Magnetic Resonance System operatively coupled with a means for deconvolution of the two-dimensional total correlation spectroscopy spectrum.

2. The method of claim 1, wherein the two-dimensional total correlation spectroscopy spectrum comprises a two-dimensional time-proportional phase incrementation total correlation spectroscopy dataset.

3. The method of claim 2, wherein the covariance processing of the two-dimensional time-proportional phase incrementation total correlation spectroscopy dataset comprises:
    Fourier transforming the two-dimensional time-proportional phase incrementation total correlation spectroscopy dataset along a direct dimension $t_2$;
    phase- and baseline- correcting the two-dimensional time-proportional phase incrementation total correlation spectroscopy dataset;
    identifying and eliminating at least one dispersive part from the two-dimensional time-proportional phase incrementation total correlation spectroscopy dataset; and
    subjecting the two-dimensional time-proportional phase incrementation total correlation spectroscopy dataset to singular value decomposition to determine the matrix square-root of the covariance spectrum (C).

4. The method of claim 1, wherein the two-dimensional total correlation spectroscopy spectrum comprises a two-dimensional States-time-proportional phase incrementation total correlation spectroscopy dataset.

5. The method of claim 4, wherein the covariance processing of two-dimensional States-time-proportional phase incrementation total correlation spectroscopy dataset comprises:
Fourier transforming cosine and sine $t_1$ modulated parts of the two-dimensional States-time-proportional phase incrementation total correlation spectroscopy dataset along a direct dimension $t_2$;
phase-correcting the Fourier-transformed cosine and sine $t_1$ modulated parts of the two-dimensional States-time-proportional phase incrementation total correlation spectroscopy dataset;
identifying and eliminating at least one dispersive part from time-domain data of the two-dimensional States-time-proportional phase incrementation total correlation spectroscopy dataset;
subjecting the Fourier-transformed cosine and sine $t_i$ modulated parts of the two-dimensional States-time-proportional phase incrementation total correlation spectroscopy dataset to singular value decomposition individually; and
co-adding the Fourier-transformed cosine $t_1$ modulated part and sine $t_1$ modulated part times the imaginary unit i of the two-dimensional States-time-proportional phase incrementation total correlation spectroscopy dataset to determine the matrix square-root of the covariance spectrum (C).

6. The method of claim 1, wherein diagonal peaks of covariance spectrum are replaced by Gaussian peaks having the amplitude of the largest non-diagonal peak in the same column or row as the diagonal peaks prior to forming the overlap matrix.

7. The method of claim 1, wherein the standard peak picking comprises determining local maxima above a threshold.

8. The method of claim 7, wherein the threshold comprises a noise floor.

9. The method of claim 1, wherein the final set of magnitude traces of the individual components are identified and assigned by screening of a spectral database.

10. The method of claim 1, wherein the two-dimensional total correlation spectroscopy spectra of the chemical mixture are recorded over a mixing time from about 60 ms to about 100 ms.

11. The method of claim 1, wherein a low to medium importance index comprises an individual spin system.

12. The method of claim 1, wherein a large importance index comprises overlapping spin systems.

13. The method of claim 1, wherein the chemical mixture comprises a biological fluid.

14. A system for the deconvolution of a chemical mixture by covariance spectroscopy comprising a Nuclear Magnetic Resonance System for producing a two-dimensional total correlation spectroscopy spectrum and a means for deconvolution of the two-dimensional total correlation spectroscopy spectrum, wherein the means for deconvolution comprises a computational system operable to:
perform covariance processing on the two-dimensional total correlation spectroscopy spectra to determine a matrix square root of the covariance spectrum (C);
evaluate similarity or overlap of each row vector ($c_i$) and column vector ($c_j$) of the covariance spectrum (C) to form an overlap matrix (O) with elements ($O_{ij}$);
calculate an importance index (vector P with elements $P_i$) from the overlap matrix (O) by co-adding the elements ($O_{ij}$) of the overlap matrix (O);
identify a subset of rows of interest by applying standard peak picking to the importance index (P);
cluster the subset of rows of interest to identify a unique set of spin systems and compounds;
display the unique set of spin systems and compounds as corresponding traces of the covariance matrix to create a final set of magnitude traces: and
identify and assign each individual component of the chemical mixture from the final set of magnitude traces.

15. The system of claim 14, wherein the two-dimensional total correlation spectroscopy spectrum comprises a two-dimensional time-proportional phase incrementation total correlation spectroscopy dataset.

16. The system of claim 15, wherein the covariance processing of the two-dimensional time-proportional phase incrementation total correlation spectroscopy dataset comprises:
Fourier transforming the two-dimensional time-proportional phase incrementation total correlation spectroscopy dataset along a direct dimension $t_2$;
phase- and baseline- correcting the two-dimensional time-proportional phase incrementation total correlation spectroscopy dataset;
identifying and eliminating at least one dispersive part from the two-dimensional time-proportional phase incrementation total correlation spectroscopy dataset; and
subjecting the two-dimensional time-proportional phase incrementation total correlation spectroscopy dataset to singular value decomposition to determine the matrix square-root of the covariance spectrum (C).

17. The system of claim 14, wherein the two-dimensional total correlation spectroscopy spectra comprises a two-dimensional States-time-proportional phase incrementation total correlation spectroscopy dataset.

18. The system of claim 17, wherein the covariance processing of the two-dimensional States-time-proportional phase incrementation total correlation spectroscopy dataset comprises:
Fourier transforming cosine and sine $t_1$ modulated parts of the two-dimensional time-proportional phase incrementation-states total correlation spectroscopy dataset along a direct dimension $t_2$;
phase-correcting the Fourier-transformed cosine and sine $t_i$ modulated parts of the two-dimensional States-time-proportional phase incrementation total correlation spectroscopy dataset;
identifying and eliminating at least one dispersive part from time-domain data of the-two-dimensional States-time-proportional phase incrementation total correlation spectroscopy dataset;
subjecting the Fourier-transformed cosine and sine $t_i$ modulated parts of the two-dimensional States-time-proportional phase incrementation total correlation spectroscopy dataset to singular value decomposition individually; and
co-adding the Fourier-transformed cosine $t_i$ modulated part and sine $t_i$ modulated part times the imaginary unit i of the two-dimensional States-time-proportional phase incrementation total correlation spectroscopy dataset to determine the matrix square-root of the covariance spectrum (C).

19. The system of claim 14, wherein a low to medium importance index comprises an individual spin system and a large importance index comprises overlapping spin systems.

20. The system of claim 14, wherein the chemical mixture comprises a biological fluid.

* * * * *